United States Patent [19]

Gevins et al.

[11] Patent Number: 4,967,038
[45] Date of Patent: Oct. 30, 1990

[54] DRY ELECTRODE BRAIN WAVE RECORDING SYSTEM

[75] Inventors: Alan S. Gevins, San Francisco; Donald Durousseau, Oakland; Joel Libove, Fremont, all of Calif.

[73] Assignee: Sam Techology Inc.

[21] Appl. No.: 398,758

[22] Filed: Aug. 25, 1989

Related U.S. Application Data

[63] Continuation-in-part of Ser. No. 287,138, Dec. 21, 1988, abandoned, which is a continuation-in-part of Ser. No. 177,681, Apr. 5, 1988, abandoned, which is a continuation-in-part of Ser. No. 942,204, Dec. 16, 1986, Pat. No. 4,736,751.

[51] Int. Cl.$^5$ .............................................. A61B 5/04
[52] U.S. Cl. ................................... 128/644; 128/731
[58] Field of Search ............... 128/639, 644, 731, 732, 128/783, 791, 802

[56] References Cited

U.S. PATENT DOCUMENTS

| | | | |
|---|---|---|---|
| 3,411,495 | 11/1968 | Casby | 128/644 |
| 3,490,439 | 1/1970 | Rolston | 128/644 |
| 3,508,541 | 4/1970 | Westbrook et al. | 128/644 |
| 4,537,198 | 8/1985 | Corbett | 128/644 |
| 4,683,892 | 8/1987 | Johansson et al. | 128/644 |
| 4,709,702 | 12/1987 | Sherwin | 128/731 |
| 4,736,751 | 4/1988 | Gevins et al. | 128/731 |

Primary Examiner—Max Hindenburg
Assistant Examiner—John P. Lacyk

[57] ABSTRACT

In a medical electroencephalographic EEG system, a hat is placed on the head of the patient. The hat contains a plurality of electrodes conforming to the hat. A circuit board having a low-noise integrated circuit amplifiers may be mounted thereon. In one embodiment each of the electrodes has a number of flexible and elastic fingers, for example 2–16 gum rubber fingers, having a conductive tip at the end of each finger; or flexible fingers made entirely of conductive material. In another embodiment the multi-contact electrode uses fingers which are rigid and connected to a spring-loaded plate. The tips contact the patient's scalp, without conductive gel or liquid, to provide a redundancy of contacts.

20 Claims, 12 Drawing Sheets

DRY ELECTRODE BRAIN WAVE RECORDING SYSTEM

This application is a continuation-in-part application based in part on Application Ser. No. 287,138, filed Dec. 21, 1988, now abandoned, which was a continuation-in-part based in part on Application Ser. No. 177,681, filed Apr. 5, 1988, now abandoned, which was a continuation-in-part based in part on Application Ser. No. 942,204 for "Brain Wave Source Network Location Scanning Method and System", filed Dec. 16, 1986, now U.S. Pat. No. 4,736,751, issued Apr. 12, 1988.

BACKGROUND OF THE INVENTION

1. Field of the Invention

The present invention relates to medical devices and more particularly to an improved electroencephalogram (EEG) brain wave detection scalp electrode system.

2. Description of the Related Art

Conventional techniques for recording brain waves (electroencephalograms or EEGs) of a human subject require attaching electrodes to the scalp with a low impedance connection. This involves cleaning and abrading the scalp and applying a conducting gel or solution which makes the electrical contact between the scalp and the electrode. When performed manually, the procedure takes about 20 minutes for the 19 electrodes usually used in clinical EEG examinations. Computerized EEG systems are tending towards a larger number of channels in order to better sample the brain spatially, but are limited by the increased time and effort required to apply the electrodes. For example, the most advanced research EEG systems employ 128 electrodes which takes a team of technicians more than an hour to apply.

A prior attempt to automate EEG electrode application, by Johansson, Eralp and Itil (U.S. Pat. No. 4,683,892) is based on an electromechanical design which mechanized the manual scalp preparation procedure resulting in a complex, large and expensive apparatus.

This device, which looks like a hair dryer with 16 cylindrical protuberances, uses air pressure to push electrodes into contact with the scalp and pumps which dispense, and then retract, a cleaner and then dispense an electrode gel. The device, due to its bulk, mechanical complexity and expense, is not suitable for many application such as ambulatory monitoring, sleep studies, flight simulators, cockpits or field use.

In U.S. Pat. No. 4,709,702 to Sherwin, the electrodes contact the scalp with "tulip probes" having sharp points to "penetrate the dead skin layer". Such a sharp pointed tip is medically dangerous due to the dangers of infection and hurting the patient.

OBJECTIVES AND FEATURES OF THE INVENTION

It is an objective of the present invention to detect the brain waves of a patient at his scalp by the use of dry electrodes which touch the scalp and without the use of conductive gels or liquids.

It is a further objective of the present invention that a single electrode or a large set of such electrodes, for example, 19, may be located on the patient's scalp rapidly, with little or no preparation of the scalp.

It is a still further objective of the present invention that the placement and removal of the electrodes on the scalp should be painless and that the electrodes should not abrade the skin or puncture the skin.

It is a still further objective of the present invention that the signal amplification be located close to the detecting electrodes to prevent distortion or loss of brain wave signals.

It is a feature of the present invention to provide an electrode hat to detect brain waves from the scalp of a patient in an electroencephalogram (EEG) system. One embodiment is a stretchable and elastic fabric hat which is adapted to stretch and fit tightly on the head of the patient. A flexible circuit board means is in contact with the hat and conducts the brain wave signals. A plurality of electrodes is mounted on the hat by, for example, snaps. Each electrode comprising a plurality of non-conductive elastic flexible fingers each having a free end portion; the fingers, for example, are of gum rubber. A conductive tip is positioned at the end of each finger free end portion and the tip is adapted to contact the scalp of the patient. Conductive means (a wire) conducts brain wave signals from the tip to the circuit board means. Amplifier means, mounted on the circuit board means, amplifies the brain wave signals.

Further features of the present invention are that the fabric hat consists of pieces of fabric which are sewn together to form a helmet-shaped hat; a single electrode may be used or a plurality of electrodes and the flexible fingers of each electrode are at least four fingers and no more than sixteen fingers.

In other embodiments the hat is a helmet, such as an airplane pilot's flight helmet. The electrodes may have a plurality, for example, four, rigid fingers made of conductive material which extend from a spring-loaded plate.

SUMMARY OF THE INVENTION

In accordance with the present invention, there is provided a method and apparatus, called a "Smart Hat" to detect a patient's brain waves without the use of conducting liquids, gels or pastes, and with little or no preparation of the scalp. The "Smart Hat" avoids the problems of electromechanical devices by using novel electronically buffered, multicontact dry electrodes which do not use conducting gels, pastes or liquids, and which require little or no preparation of the scalp. In one embodiment, the system consists of from 1–256 multicontact electrodes mounted to the inner surface of a stretchable fabric hat. Each multicontact electrode has between 4 and 6 electrode contacts. Each of 4 electrodes plugs into a Field Effect Transistor (FET) input preamplifier circuit mounted on a flexible printed circuit (PC) board. The PC board is attached to a fabric cover which fits loosely over the hat. The rubber fingers of the electrodes poke through the hair and the metal tips contact the scalp. The flexibility of the rubber base allows the electrode to adapt to the local contour of the head. The redundancy of the 4 to 16 contacts on each electrode improves the electrical connection since it is not dependent on the impedance at a single small point.

The hat is made from a stretchable fabric which has been cut and sewn to conform to the shape of the head. Several back-and-forth and lateral motions of the hat, made with the outstretched hand over the front, back and each side of the head, causes the rubber fingers to part the hair and make contact with the scalp. The stretch (elasticity) in the fabric allows a single hat to fit a variety of head shapes and sizes.

An analog embodiment of the Smart Hat records and preamplifies EEG's with multicontact active dry electrodes and then carries the analog signals off the head with a ribbon cable to the input of a commercial clinical EEG amplifier system. A digital version of the Smart Hat further amplifies, filters and digitizes the brain signals and translates them to an optical form for transmission to a decoding circuit located on a parallel interface card of a computer.

The Smart Hat has high noise immunity and is very simple to apply. It yields signals whose quality is at least as good as those recorded with conventional wet cup (gel) EEG electrodes and amplification electrodes. In the digital embodiment, individual analog-to-digital (A/D) converters for each channel and optical isolation of the entire hat provide the highest signal fidelity. for monitoring the electrical activity of the brain.

The Smart Hat is applicable to clinical and research situations

BRIEF DESCRIPTION OF THE DRAWINGS

The following detailed description should be taken in conjunction with the accompanying drawings, in which.

DETAILED DESCRIPTION OF THE INVENTION

Figure 1:
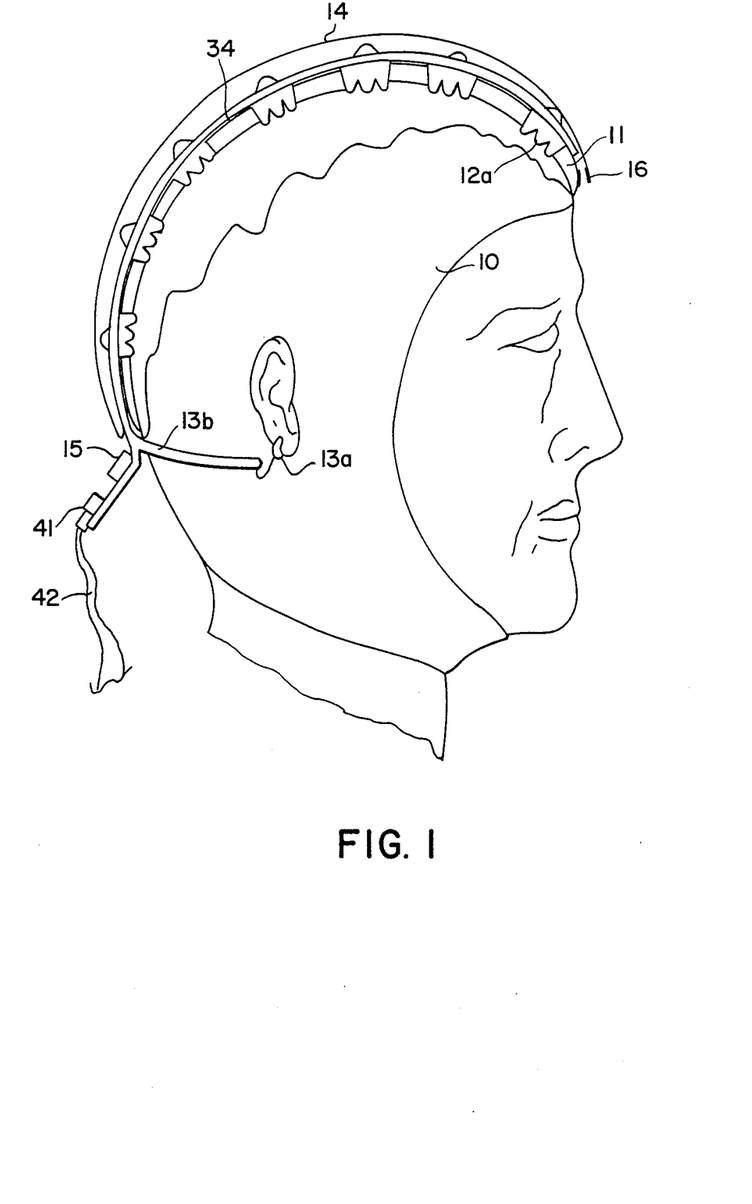
FIG. 1 is a side plan view in which the EEG hat of the present invention is shown in cutaway side plan, FIG. 1 being the analog embodiment of the hat.

In use, an active electrode EEG Smart Hat is placed on the head of the patient to detect the patient's brain waves. As shown in FIG. 1, preferably the hat 10 includes a stretchable cloth hat body 11 having 1 to 256 rubber multicontact electrodes 12a-n. The designation "n" means that the number depends on the number of electrodes (channels) desired, for example, n may be in the range 1 to 256. The hat body 11 is made from a stretch (elastic) fabric which is 50% lycra and 50% cotton.

Figure 2:
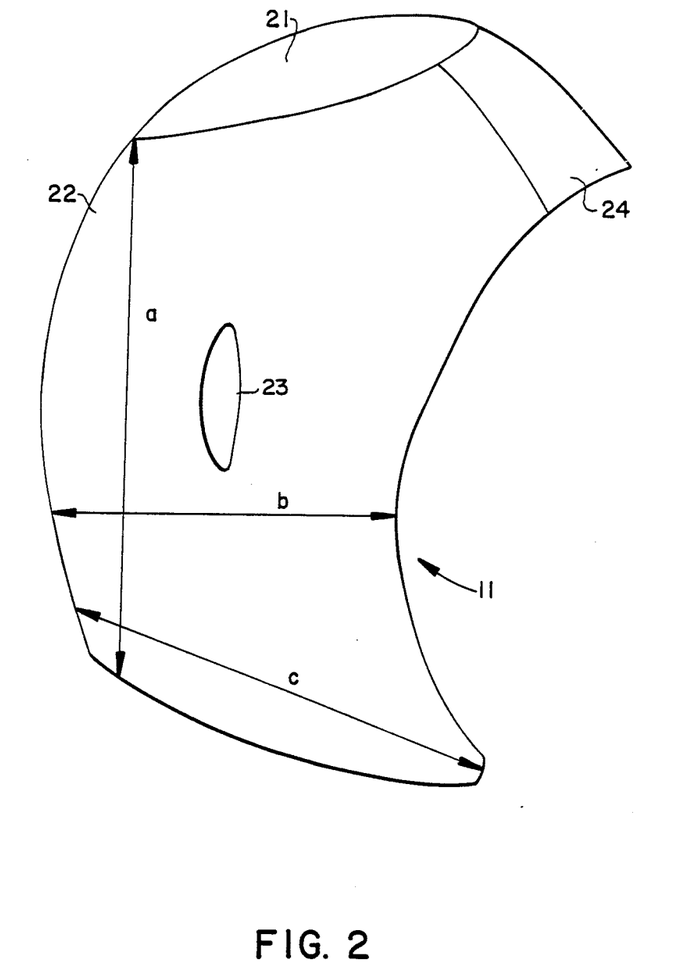
FIG. 2 is a side plan view of the construction of the stretch fabric body of the hat of FIG. 1.
Figure 3A:
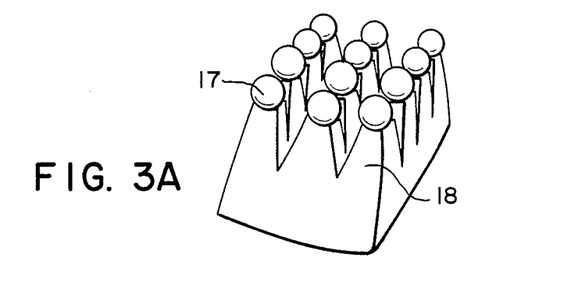
FIG. 3A is a perspective picture of the multicontact dry EEG electrode of the present invention.
Figures 3B, 3C:
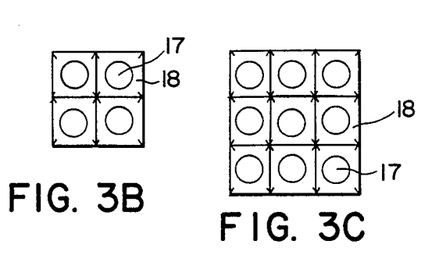
FIGS. 3B-3E are top plan views of embodiments of the multicontact electrode of the present invention, showing configurations with 4, 9, 12 and 16 metal tips.
Figure 3D:
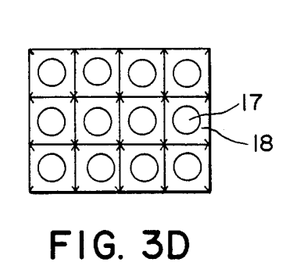
Figure 3E:
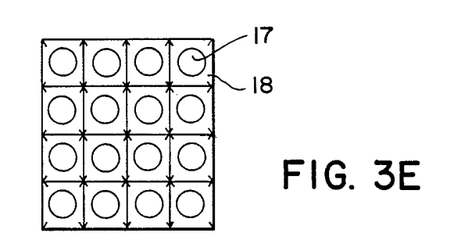

As shown in FIG. 2, the fabric hat body 11 is preferably constructed out of 4 pieces of fabric. The top piece 21 is oval, shaped to sit on the relatively flat part of the head, and is 15 cm×9 cm. The two side pieces 22 are attached to the top piece 21 by cotton thread and are sewn to each other in the back. Each side piece 22 has a hole 23 cut for the ear. The dimensions of the side piece, as shown in FIG. 2, are: length of a is 18 cm, length of b is 19 cm and length of c is 21 cm. The side pieces 22 snap together underneath the chin. The front piece 24 covers the forehead and is sewn to the side and top pieces and is 10 cm by 7 cm. The dimensions listed are for an average adult head. Proportionally smaller sizes are used for children's heads. The stretchable fabric conforms to heads of different sizes and shapes. The hat body 11 is held down on the head by the extensions to the side pieces which snap together under the chin. The stretch of the fabric allows it to fit a variety of head sizes and shapes. To keep hair preparation products from interfering with the contact between the electrodes and the scalp, the subject's hair should be clean and briefly brushed with a stiff plastic bristle brush prior to putting on the hat. Several back-and-forth lateral motions of the hat, made with the outstretched hand over the front, back, and each side of the head, cause the rubber fingers to part the hair and make a contact between the metal tips and the scalp.

Figure 4:
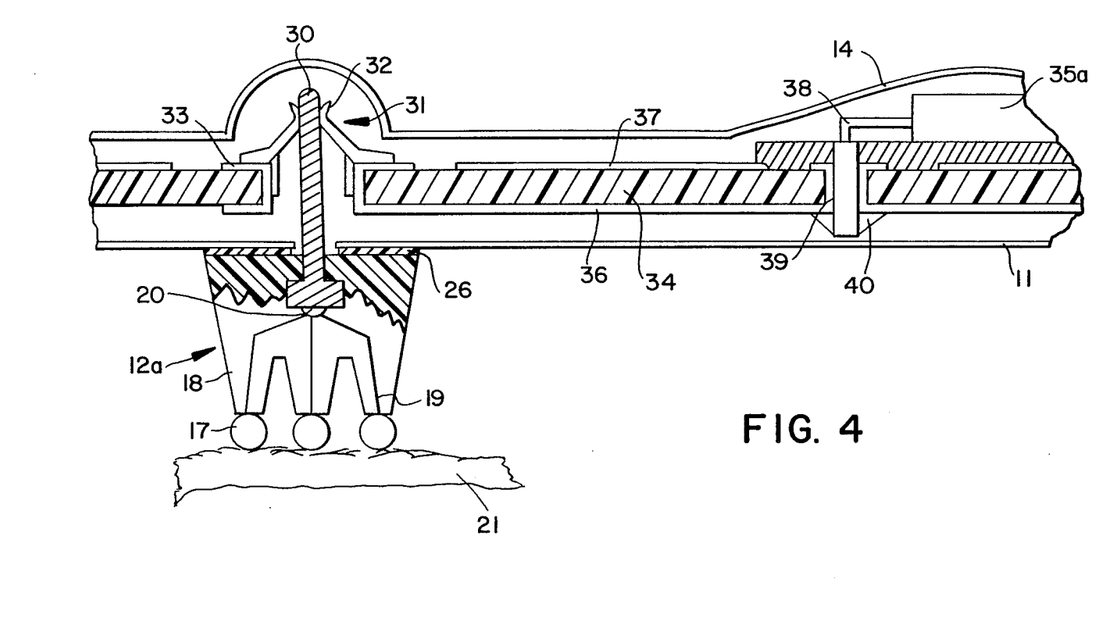
FIG. 4 is an expanded cutaway side view of the hat showing the electrodes, preamplifiers and the flexible printed circuit board.

As shown in FIGS. 3 and 4, each of the electrodes 12a consists of a pure gum rubber block, 1.0 to 2.5 cm square with four to sixteen metal tips 17 at the end of 0.5 to 1.0 cm pyramid-shaped rubber fingers 18. Wires 19 are threaded down the center of each finger and are soldered to the metal tip. The tip consists of a 2-mm tin-lead (60-70% tin, 30%-40% lead) ball. At the upper end of the electrode, the wires are soldered to a gold plated pin 30 which plugs into a connector on the flexible printed circuit board. The rubber base of each electrode is attached to the fabric hat with 1 to 4 plastic snaps 26. The flexibility of the rubber base allows the multiple fingers to adapt to the local contour of the head. The redundancy of multiple contacts improves the connection since it is not dependent on the impedance at a single small point.

Figure 5A:
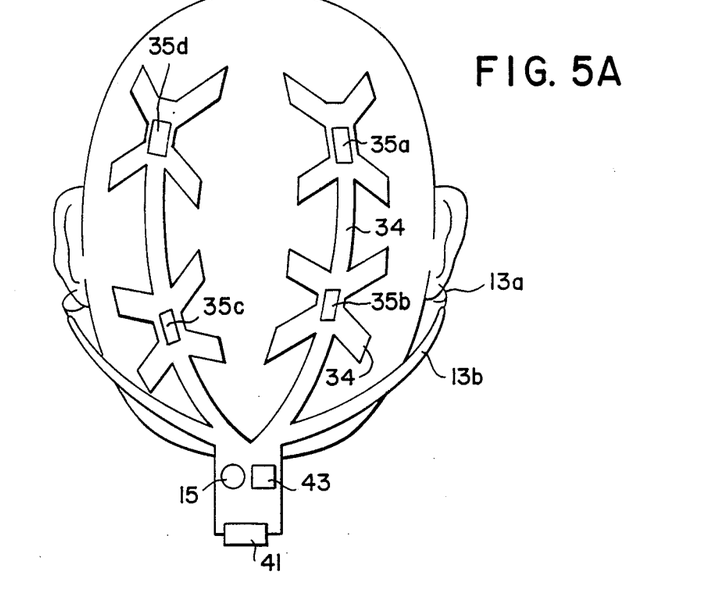
FIG. 5A is a top view of the hat with cover removed to show the flexible printed circuit boards and preamplifier circuits.
Figure 5B:
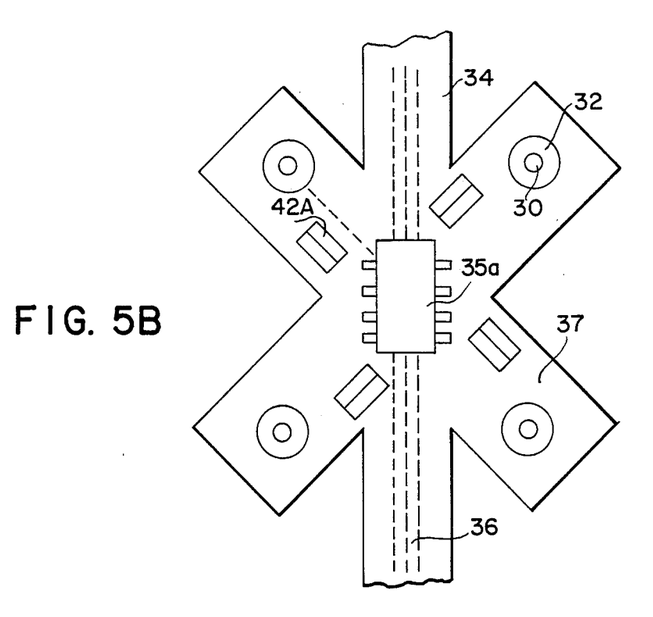
FIG. 5B is an enlarged view of a portion of FIG. 6.

As shown in FIGS. 4 and 5, a gold-plated metal pin 30 from each of the electrodes plugs into a contact spring receptacle 31 having a pair of gold-plated spring contacts 32. The receptacle is attached to a metal pad (with a plated-through hole) on the flexible non-conductive printed circuit board 34. Conductors 36, which are copper foil signal traces, conduct the signals from each electrode 12a-12n to a nearby preamplifier circuit 35a. The flexible printed circuit board 34 is preferably composed of a polyamide material having a copper foil ground plane 37 on the top side and signal trace conductors 36 on the bottom side. The ground plane 37 serves to shield the signal traces and electrodes from pickup of stray noise. The hat 10 employs 1 to 64 quad FET input (field effect transistor), amplifier integrated circuits 35a-n such as the Maxim ICL7642, for low-noise analog preamplification of the microvolt EEG signals by a factor of 100 to a 10 mV range. Each amplifier services four electrodes. Two resistors 42 determine the gain of the preamplifier circuit. Each integrated preamplifier circuit 35a-n is soldered by solder 40 to the flexible printed circuit board 34 using an amplifier input lead 38 and a pad 39 with plated-through hole.

As shown in FIGS. 3A-3E and 4, each of the electrodes 12a-n includes a plurality of flexible fingers. The electrode 12a has nine flexible fingers 18 (preferably of gum rubber), but only three of which are shown in FIG. 4. The embodiment of FIG. 3A has twelve flexible fingers 18; the embodiment of FIG. 3B has four flexible fingers 18 (1.0 cm×1.0 cm); the embodiment of FIG. 3C and FIG. 4 has nine flexible fingers 18 (1.5 cm×1.5 cm); the embodiment of FIG. 3D has twelve flexible fingers 18 (2.0 cm×1.5 cm); and the embodiment of FIG. 3E has sixteen flexible fingers 18 (2.5 cm×2.5 cm). As shown in FIG. 4, each of the electrodes 12a-n has a plurality of conductive round metal tips 17, each finger 18 terminating in a conductive tip 17. A metal flexible wire 19 runs from each tip to a conductive metal solder 20 attaching the wires 19 to the bottom of the pin 30. The tips 17 contact the scalp 21.

As shown in FIG. 5, the flexible printed circuit board 34 conducts signals from the outputs of the preamplifier circuits 35a-n (circuits 35a-d being shown in FIG. 5) to a common point at the back of the head where a connector 41 to a flat ribbon cable (42 shown in FIG. 1) conducts the signals off the head. Power for the preamplifiers is provided by a battery pack 15 located at the back of the head and consists of 2 batteries such as Electrochem Industries 3B50. Ear clip reference electrodes 13a plug in to extensions 13b to the printed circuit board 34. An amplifier circuit 43, located at the back of the head, amplifies and adds together the signals from the reference electrodes.

In order to allow the stretchable cap to adapt to the head shape of each patient, slack is allowed in the printed circuit board between each arm of each four-electrode cluster, as well as between clusters and the collection point at the back of the head. The printed circuit board is attached to the hat cover 14 with plastic snaps. The cloth hat cover 14 attaches to the stretchable hat body 11 with a Velcro (TM) rim 16. For cleaning, each electrode is unplugged from the printed circuit board, and the stretchable cap and electrodes are separated as a unit from the hat cover and printed circuit board.

Figure 6:
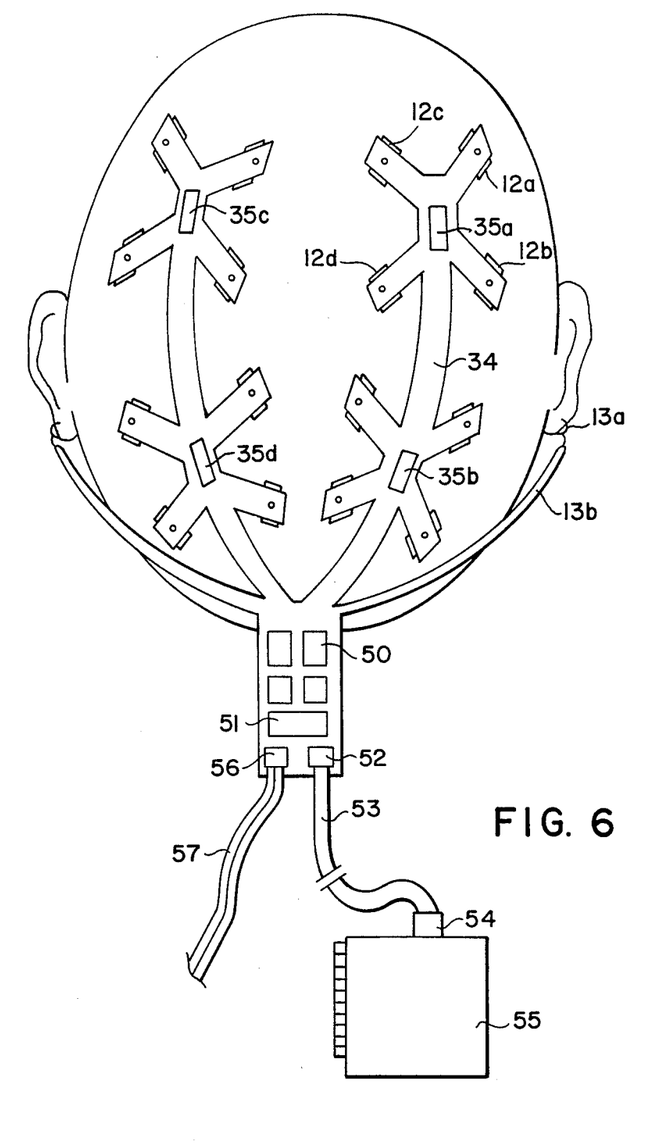
FIG. 6 is a top view of the digital embodiment of the hat with cover removed, to show the encoder chips, digital multiplexing circuitry, fiber optic transmitter, and decoder circuit board.

As shown in FIG. 6, the digital embodiment of the Smart Hat has several components in addition to those of the analog embodiment described above. In the digital embodiment of FIG. 6, (1) From 1 to 16 encoder circuits 50 each perform filtering, amplification, digitization, and multiplexing of the outputs from the preamplifier circuits. Each encoder circuit services 16 channels;

(2) A digital multiplexing circuit 51 multiplexes the outputs of the encoder circuits;

(3) A fiber optic transmitter 52 translates the output of the digital multiplexing circuit to a stream of light pulses;

(4) A fiber optic cable 53, fiber optic receiver 54, and decoder circuit 55 to translate from light to digital form, demultiplexes the signal and converts the signals into a parallel bit stream readable by a computer.

Additionally, the battery pack (not shown) is located in a pad worn across the shoulder and consists of 4 Alkaline D cells which are connected to connector 56 by cable 57.

As shown in FIG. 6, the encoding circuits are preferably mounted on the hat which requires that electronics for each group of 16 channels be implemented with a custom integrated circuit for simplicity and small physical size. If active circuitry is placed off the hat, commercially available IC's may be used. The decoder circuit 55 is contained on a printed circuit board which resides in the data analysis computer.

Figure 7:
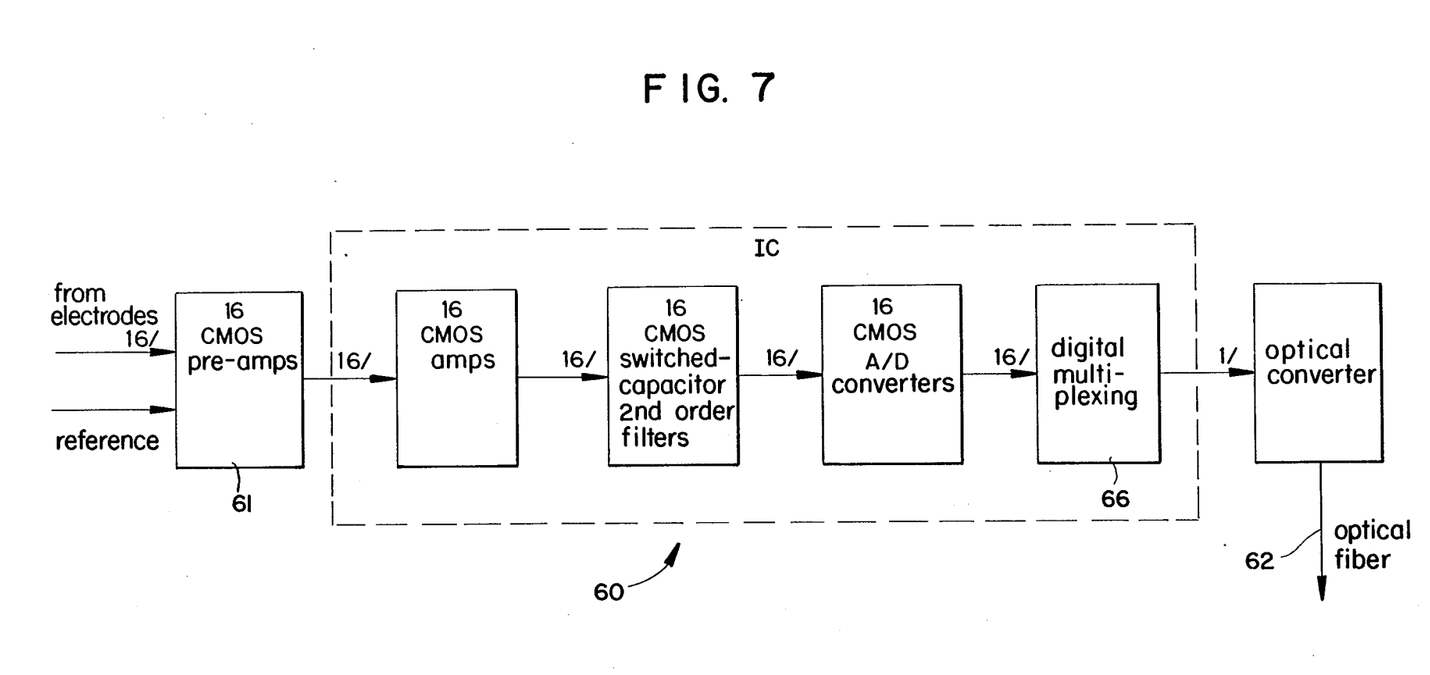
FIG. 7 is a block diagram of the encoder circuit.

As shown in FIG. 7, the preferred IC implementation of the encoder circuit employs a sigma-delta A/D on each chip, resulting in a high-rate (512 Kbit/sec) one-bit digital output from each chip. This implementation has better noise immunity in unshielded enviroments. The essence of the electronics design is a semi-custom LSI integrated circuit 60 which converts preamplified EEG volts from 16 channels, i.e., from CMOS pre-amps 61, to an oversampled bit stream using switched-capacitor filters and sigma-delta converters. The voltages are picked up at the scalp using the aforementioned metal-tipped, multicontact rubber electrodes 12a-n, preamplified using the aforementioned commercial FET input amplifiers 35a-n, and then amplified, filtered and converted using circuit 60 which is preferably implemented in a semi-custom IC based on standard commercially available IC building blocks. An optical fiber 62 is used to carry the final multiplexed signal from the hat to a decoder circuit located nearby.

The IC 60 performs amplification by a factor of about 100, antialiasing filtering provided by the combination of a fixed RC pole at 128 Hz and a variable 2nd-order switched-capacitor biquad filter, sigma-delta conversion to an oversampled bit stream at a rate 64 times the Nyquist rate (16,384 Hz for 128 Hz bandwidth data), and multiplexing to a single 1-bit channel. The sampling rate and corresponding filter cutoff is proportional to the frequency of the clock signal supplied to the switched capacitor filters. The latter will be variable from 32 to 128 Hz. The six octave oversampling means that the two-pole filter attenuates by roughly 72 dB at half the sampling frequency. The gain and filtering is accomplished by a single switched-capacitor filter circuit which uses two standard parasitic-insensitive switched-capacitor integrators. The sigma-delta circuit also uses two switched-capacitor integrators, but also requires a simple comparator to do the single-bit digitization. The outputs of sixteen channels are multiplexed (digital multiplexing 66) with a standard digital circuit design. All circuits are designed and fabricated in a CMOS process, which makes good capacitors, and integrating amplifiers, and can be easily designed for lower power consumption.

Figure 8:
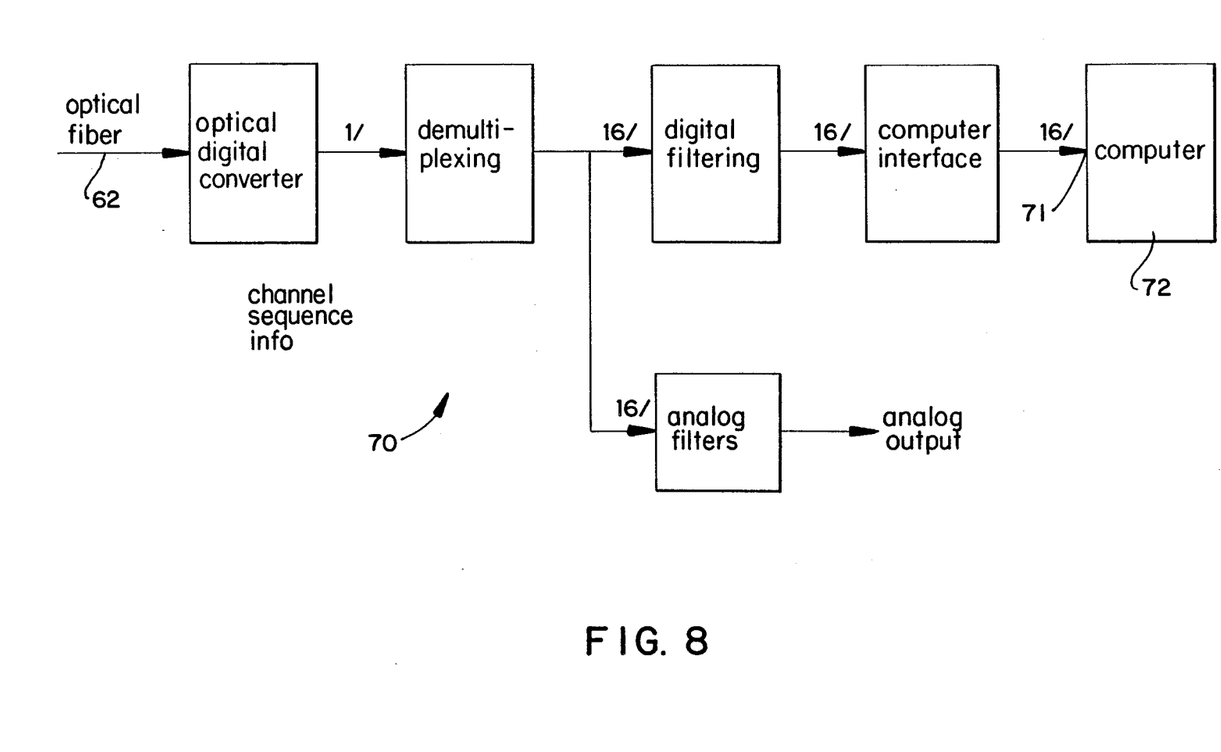
FIG. 8 is a block diagram of the sigma-delta decoder.

As shown in FIG. 8, the decoder circuit 70 demultiplexes the high-rate bit stream from optical fiber 62 into 12-bit representations of each of the signal channels, and makes the data available to a parallel input port 71 of a computer 72.

Each of the sixteen amplification/filtering/quantization modules on the chip 60 is a complete unit with connections only at the input and output. Gain, filtering and digitization sections have no interconnections between channels. This greatly simplifies IC design and layout, interconnect is essentially only within the area allotted for each channel. Each channel is essentially an independent module which can be separately charaterized and simulated. This simplicity also implies that a single level of metallization is sufficient for the design, which permits use of well-proven CMOS IC processes. A post-processing circuit translates multiplexed digital signals in two's complement 12-bit binary form, which are stored on a computer.

Figure 9:
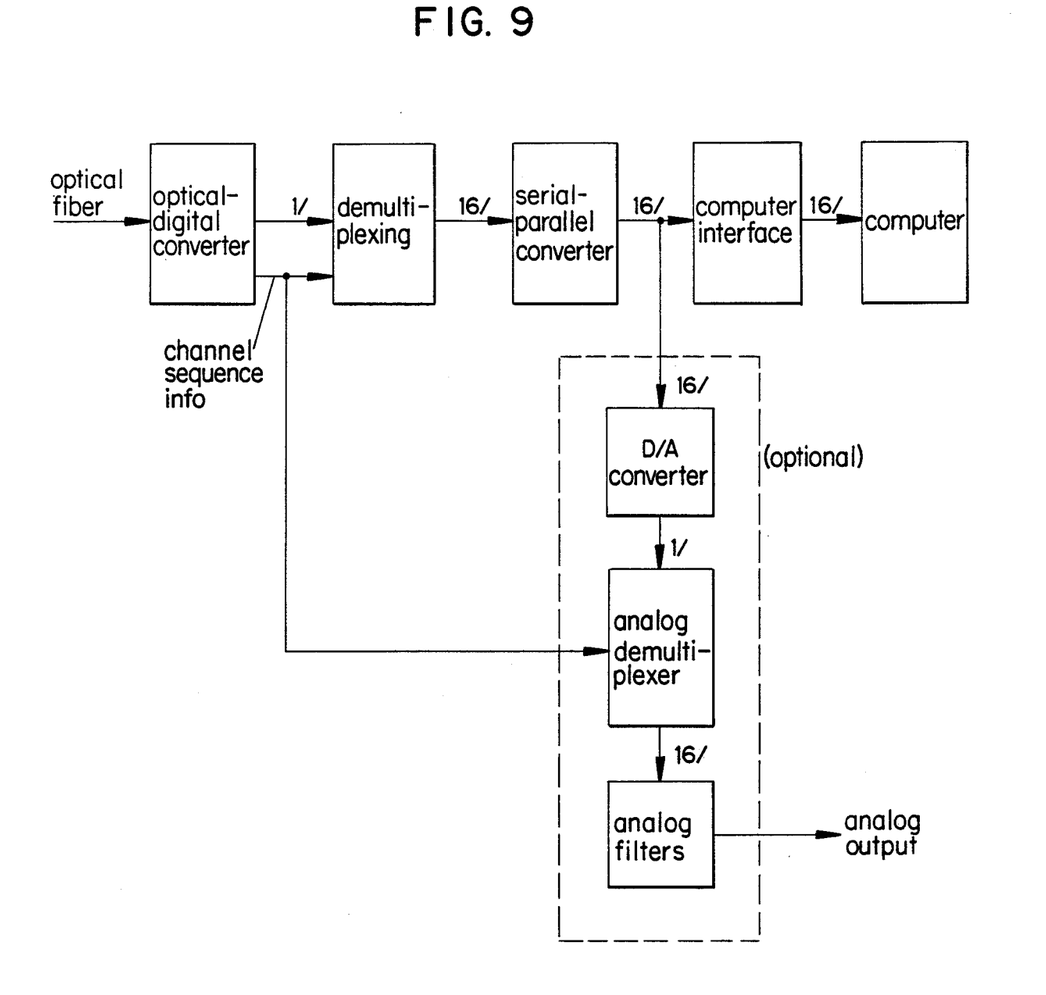
FIG. 9 is a block diagram of the offset binary decoder.

An alternative embodiment of the digitally multiplexed hat uses 16 12-bit integrating A/D converters (as opposed to delta-sigma converters) to generate full offset binary directly. FIG. 9 shows the decoder circuit for this alternative embodiment. This requires one additional 12-bit counter per channel on the IC, and necessitates digital to analog (D/A) circuitry in the decoder circuit to retrieve the analog signal.) In applications requiring digital output only, the availability of low-bit-rate binary code without additional digital filtering is advantageous. The demultiplexing can also be at a lower rate in this instance.

Although the above-described embodiments relate to a stretchable fabric hat, the multi-finger elastic electrodes of the present invention may be mounted within a stiff plastic helmet ("Smart Helmet"), for example, a pilot's flight helmet. The circuit board, in that case, need not be flexible but may be molded and curved to fit inside the helmet. The electrodes are mounted on a soft liner mounted in the helmet, and the signals conducted to the preamplifier and amplifier circuits attached in the helmet by snaps or other fasteners. The elastic material of the fingers 18 may be made of natural or synthetic rubber foam, or other suitable elastomeric rubber-like polymers.

Figure 10:
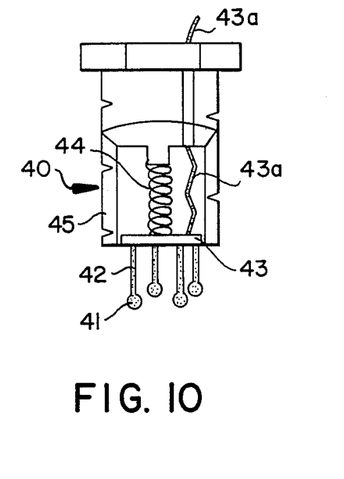
FIG. 10 is an enlarged cross-sectional view of an alternative embodiment of an electrode assembly.
Figure 11:
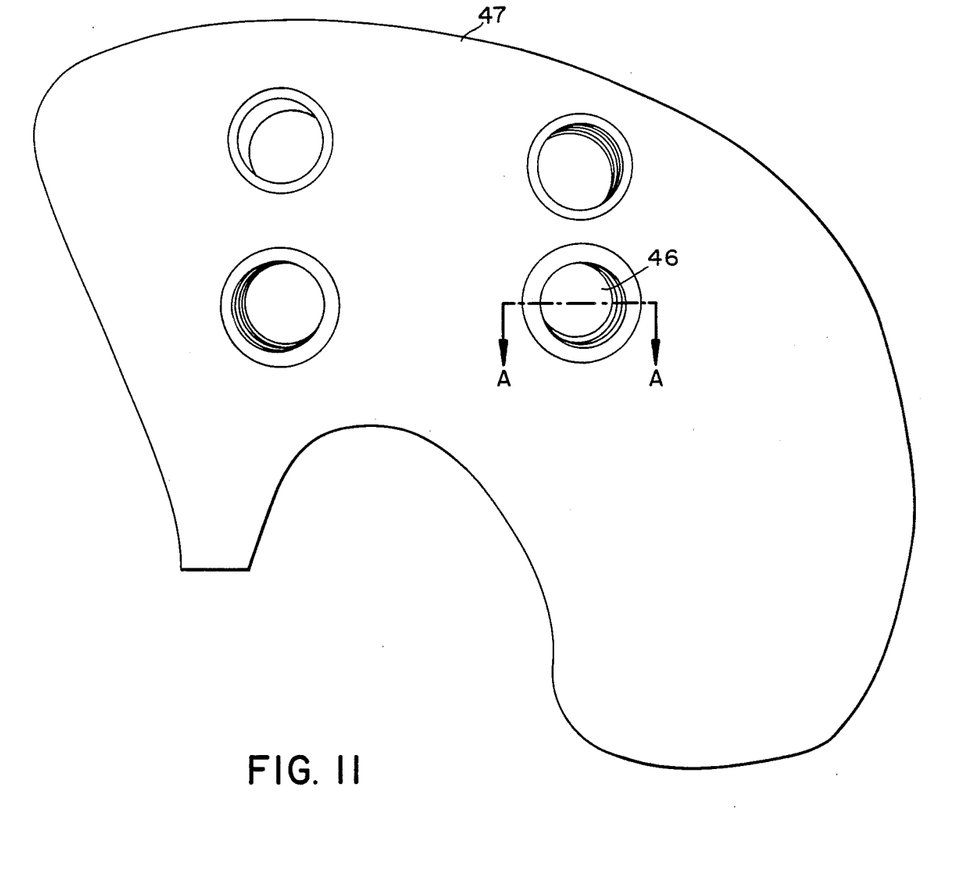
FIG. 11 is a side plan view of a semi-rigid plastic helmet having socket holes for the electrodes assemblies of FIG. 10.
Figure 12:
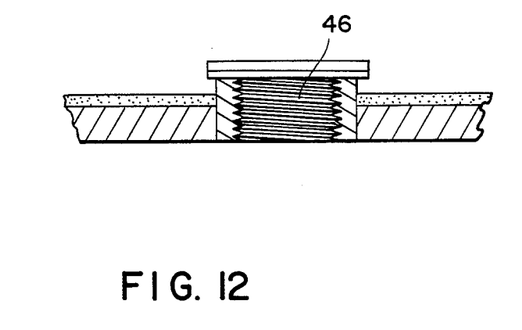
FIG. 12 is an enlarged cross-sectional view along line A—A of FIG. 11 showing the socket boss for holding the electrode and for electrode adjustment.

Another embodiment is shown in FIGS. 10–12, which shows a single electrode 40, which is one of a series of similar spring-loaded multi-contact electrodes mounted in a semi-rigid helmet. The electrode 40 is a 2-cm, cylindrical, spring-loaded multi-contact plastic dry electrode. Electrode 40 consists of four 3-mm metallic ball tips 41 each at the end of a 1.5-cm metallic rigid shaft 42 attached to a rigid conductive mounting plate 43. The plate 43 is spring-loaded by spring 44, within a plastic housing 45, to provide equal pressure to the multiple contact tips 41. To accommodate a variety of head sizes and shapes, the long, soft spring 44 applies a constant load normal to the scalp relatively independent of its deflection. Lead 43a is connected to plate 43. The electrodes 40 are adjustably mounted by external threads to move each electrode in and out within screw holes 46 in a semi-rigid formed plastic shell 47, see FIGS. 11 and 12. The plastic shell 47 maintains the electrodes at the proper angle for good contact with the scalp. In this embodiment, shown in FIGS. 10–12, the multi-contact dry electrode has electrode shafts attached to a rigid spring-loaded plate. Rotating the outer housing 52 clockwise in hole 46 achieves gross alignment of the electrode assembly with the head. The soft spring 44 applies pressure, bringing the electrode tips 41 in contact with the scalp.

Figure 13A:
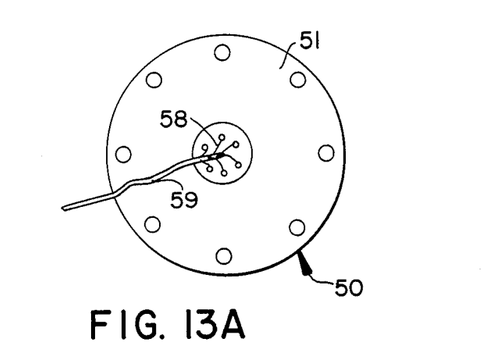
FIG. 13A is a top plan view of an electrode embodiment using radial flexure springs.
Figure 13B:
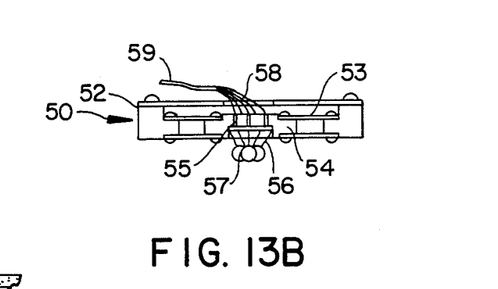
FIG. 13B is a side cross-sectional view of the embodiment of FIG. 13A.
Figure 13C:
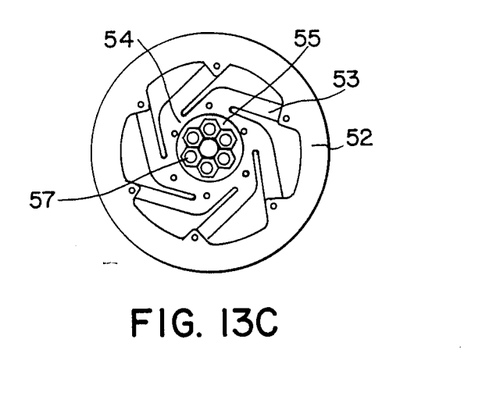
FIG. 13C is a bottom plan view of the embodiment of FIG. 13A.

Another embodiment is shown in FIGS. 13A–13C, which shows a single flat electrode assembly 50. A plurality of electrode assemblies is used in a helmet. The flat electrode assembly 50 consists of (1) a backing plate 51 used for attachment and stability; (2) a plastic housing 52 to provide for mounting the flat radial flexure spring 53; and (3) an internal plate 54 which attaches to the spring 53 and allows the mounting plate 55 holding the rigid electrode fingers 56 and tips 57 to snap-lock into place. The mounting plate 55 with multiple electrode contact tips 57 is preferably manufactured as a single unit so that it is removable for cleaning or repair. The tips 57 and fingers 56 are conductive, preferably a noble metal-plated metal, and are connected by wires 58 to electrode lead 59.

Figures 14A, 14B, 14C, 15A, 15B, 15C, 15D, 15E:
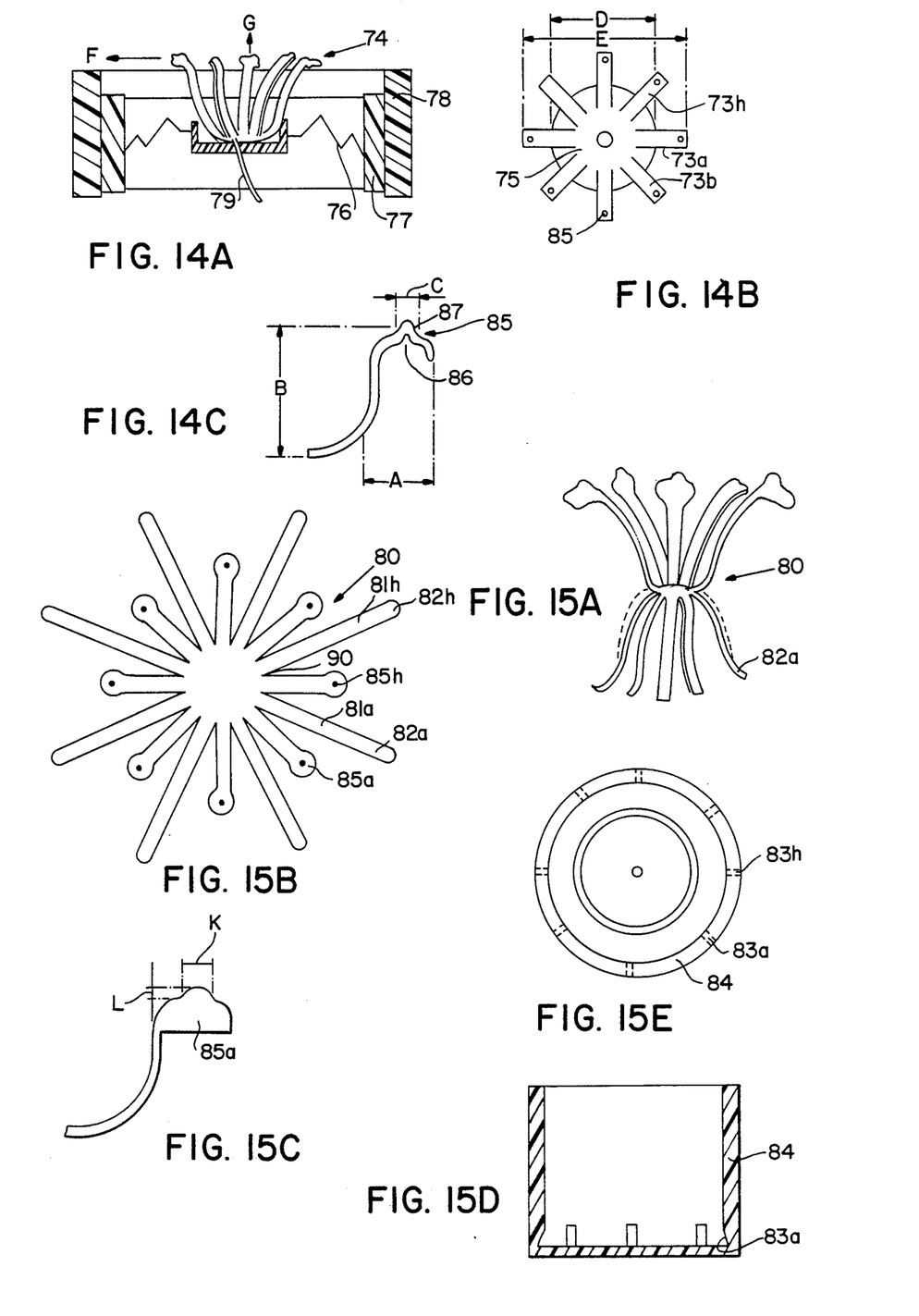
FIG. 14A is a side cross-sectional view of an alternative electrode assembly.
FIG. 14B is a top plan view of the electrode of the embodiment of FIG. 14A as a flat sheet prior to being formed into an electrode.
FIG. 14C is an enlarged side plan view of an electrode free end of the embodiment of FIG. 14A.
FIG. 15A is a perspective view of the electrode of another embodiment of an electrode assembly.
FIG. 15B is a top plan view of the electrode of FIG. 15A as a flat sheet prior to being formed into the electrode of FIG. 15A.
FIG. 15C is an enlarged side plan view of an electrode free end of the embodiment of FIG. 15A.
FIG. 15D is a side cross-sectional view of the plastic electrode holder of the embodiment of FIG. 14A.
FIG. 15E is a top view of the electrode holder of FIG. 15D.

In the embodiment shown in FIGS. 14A–14C the electrode fingers (prongs) $73a$–$73h$ are formed from a flat sheet of metal, preferably a beryllium-copper alloy which is gold-plated, see FIG. 14B. The fingers, at their free end tips 85 are curved in an inverted U-shape 86 and formed with a protruding dimple 87, see FIG. 14C. Preferably each dimension "A" is ⅜-inch; the dimension "B" is 0.6-inch; the dimension "C" is ⅛ (diameter); and in FIG. 14B the dimension "D" is 0.5-inch and the dimension "E" is 1.2-inch. The tips 74, when they are applied to the scalp, will be pushed outwardly (direction of arrow "F", FIG. 14A) so that the tips spread the hair and touch the skin. Generally, contact with the skin is at the dimples.

The flat base 75 of the electrode 74 is held in a cavity in a plastic spring 76. The spring 76 is similar to a bellows and, when compressed, urges the electrode 74 toward the scalp in the direction of arrow G (FIG. 14A). The plastic spring 76 is a disk membrane which is held at its circumference in plastic ring (housing) 77 which is slidingly held in plastic ring electrode holder 78. The electrode 74 is connected, by a flexible wire 79, to the flexible circuit board. The electrode holders 78, like the electrode holders previously described, are preferably mounted in a helmet or a stretch hat. In use, the housing 77 may be pushed toward, or away from, the patient's scalp to position the electrode assembly.

The embodiment of the electrode assembly illustrated in FIGS. 15A–15E is similar in many respects to the embodiment of FIGS. 14A–14C, except that the spring force in the embodiment of FIGS. 15A–15E is from metal springs which are integral with the electrode. As shown in FIG. 15B, the electrode 80 is formed from a flat metal sheet 90, preferably a berylluim-copper alloy, which is gold-plated. The legs $81a$–$81h$, under pressure, will bow upwardly, as shown by the dash-dash lines of FIG. 15A. The feet $82a$–$82h$ (bottom free ends) fit and are held in slots $83a$–$83h$ of the plastic electrode holder 84. The electrode prong, in this embodiment, has the following dimensions: dimple diameter "K" of ⅛-inch; "L" height of dimple 0.1-inch, see FIG. 15C. The other dimensions are as in the embodiment of FIG. 14C.

The tips make contact with the skin of the scalp by being pushed out from the imaginary center of the electrode and pushing the hair away from the contact spot.

The electrodes of FIGS. 14A-14C and 15A-15E are preferably mounted in the helmet structure of FIG. 11 or in the aforementioned stretch hat and are used along with the flexible printed circuit boards described above. The plastic holders of FIGS. 14A-14C and 15A-5E provide electrical isolation for their electrodes and permit adjustment of the electrode position by moving the holder within the helmet either toward, or away from, the scalp.

In all the embodiments each of the electrodes have at least 2, and preferably 6-10, tip means to make electrical contact with the scalp without abrading or hurting the scalp. The tip means includes a conductive tip which is preferably rounded. Each tip has a diameter "A", see FIG. 14C, greater than 0.1-inch and preferably in the range of 0.15-0.3-inch and a maximum of 2 inches. The preferred radius of curvature on the dimpled nipple is at least 0.05-inch and preferably in the range of 0.1-0.15-inch. Each tip, at its area of contact with the scalp, is non-pointed, smooth and non-abrasive to the scalp. This permits each finger to contact different skin regions without injury or discomfort to the scalp. The size of the electrode is such that the spatial separation between the tips is sufficient to sample several spots within a small region of the scalp. This is important, for example, to ensure that all tips are not in contact with a scab or flake of dead skin or large piece of dandruff.

We claims:

1. An electrode hat to detect brain waves from the scalp of a patient in an electroencephalogram EEG system, the hat comprising:
   a hat adapted to fit on the head of the patient;
   a circuit board means within and conforming to the hat;
   a plurality of electrodes mounted on the hat, each electrode comprising a plurality of non-conductive elastic flexible fingers each having a free end portion, a conductive tip means at the end of each finger free end portion to make electrical contact with the scalp of the patient without abrading or hurting the scalp, said tip means including minimally a conductive tip to contact the scalp having a diameter of greater than 0.1-inch at its contact with the scalp, a surface which is smooth, non-pointed and non-abrasive to the scalp, and conductive means to conduct brain wave signals from the tip to said circuit board means;
   and amplifier means mounted on said circuit board means to amplify the brain wave signals.

2. An electrode has as in claim 1 wherein the hat is a stretchable and elastic fabric cap adapted to stretch and fit tightly on the head of the patient and the circuit board means is a flexible circuit board.

3. An electrode hat as in claim 1 and further including a plastic electrode holder means to be fitted on said hat and to enclose and mount each of said electrodes.

4. An electrode hat to detect brain waves from the scalp of a patient in an electroencephalogram EEG system, the structure comprising:
   a helmet adapted to fit on the head of the patient;
   at least one dry electrode mounted on the helmet to contact the scalp without liquid or gel conductive material, said electrode comprising a plurality of stiff conductive fingers each having a free end portion, a plate upon which the fingers of each electrode are mounted, spring means to spring-load said plate relative to said helmet, a tip means at the end of each finger free end portion to contact the scalp of the patient without abrading or hurting the scalp, said tip means including a conductive tip to contact the scalp having a diameter of greater than 0.1-inch at its contact with the scalp, a surface which is smooth, non-pointed and non-abrasive to the scalp, and conductive means including said fingers to conduct brain wave signals from the tips.

5. An electrode hat as in claim 4 wherein said electrode is an electrode assembly including a casing having an imaginary axis, and adjustable means to adjustably mount said casing on said helmet to adjust it along said axis.

6. An electrode hat as in claim 4 wherein said spring means is a helical coil spring.

7. An electrode hat as in claim 4 wherein said spring means is a flat spring.

8. An electrode hat as in claim 4 wherein said spring means is a bellows-like plastic spring.

9. An electrode hat as in claim 4 and further including a circuit board means within and conforming to the helmet to conduct the brain wave signals and amplifier means mounted on said circuit board means to amplify the brain wave signals.

10. An electrode hat as in claims 1 or 3 comprising a plurality of at least 4 electrodes.

11. An electrode hat as in claims 1 or 3 wherein the fingers of each electrode are at least two fingers and no more than sixteen fingers.

12. An electrode hat as in claims 1 or 3 wherein each conductive tip has a rounded free end portion.

13. An electrode hat as in claim 1 wherein the conductive means includes a flexible metal wire mounted within each of said fingers.

14. An electrode hat as in claims 1 or 9 wherein said circuit board means includes an insulative circuit board, a conductive ground plane foil adhered on one side thereof and signal trace elongated foil conductors adhered to the opposite side thereof.

15. An electrode hat as in claims 1 or 9 wherein the amplifier means includes at least one input low-noise preamplifier having FET inputs.

16. An electrode hat as in claims 1 or 9 and further including a battery and a connector on said circuit board means, said battery being connected to said amplifier means.

17. An electrode hat as in claims 1 or 9 and further including an ear clip reference electrode, a reference cable connected to said clip electrode, and a reference amplifier mounted on said circuit board means and connected to said reference cable.

18. An electrode hat as in claims 1 or 9 wherein the hat has a plurality of electrodes and said amplifier means comprises at least one integrated circuit quad amplifier.

19. An electrode hat as in claims 1 or 9 and further including an encoder circuit mounted on said circuit means, a digital multiplexing circuit mounted on said circuit board means, a fiber optic transmitter mounted on said circuit board means and an optic fiber cable connected to said optic transmitter;
   wherein said brain waves are connected to digital data, multiplexed, converted to optical signals and transmitted on said optical fiber cable.

20. An electrode hat as in claims 1 or 3 and further including, mounted on said circuit board means, an integrated circuit including a plurality of input channels and connected to each channel a multi-bit analog-to-digital converter.

* * * * *